United States Patent
Munn

(10) Patent No.: US 10,463,759 B2
(45) Date of Patent: Nov. 5, 2019

(54) DISINFECTING VANITY MIRRORS

(71) Applicant: STERILUMEN, INC., Tarrytown, NY (US)

(72) Inventor: Max Munn, Tarrytown, NY (US)

(73) Assignee: SteriLumen, Inc., Tarrytown, NY (US)

(*) Notice: Subject to any disclaimer, the term of this patent is extended or adjusted under 35 U.S.C. 154(b) by 0 days.

(21) Appl. No.: 16/057,433

(22) Filed: Aug. 7, 2018

(65) Prior Publication Data

US 2018/0361008 A1    Dec. 20, 2018

Related U.S. Application Data

(63) Continuation-in-part of application No. 15/601,607, filed on May 22, 2017, now Pat. No. 10,039,853, and
(Continued)

(51) Int. Cl.
*A61L 9/20* (2006.01)
*A61L 2/26* (2006.01)
(Continued)

(52) U.S. Cl.
CPC ............. *A61L 9/20* (2013.01); *A47B 67/005* (2013.01); *A47G 1/02* (2013.01); *A61L 2/10* (2013.01);
(Continued)

(58) Field of Classification Search
CPC .................................. A61L 2/10; A45D 42/00
(Continued)

(56) References Cited

U.S. PATENT DOCUMENTS 3,776,694 A  * 12/1973  Leittl ................... A61L 2/10
                                                      312/206
6,773,682 B1   8/2004  Benda
(Continued)

FOREIGN PATENT DOCUMENTS

CN        202526007       11/2012
CN        202629828       12/2012
(Continued)

OTHER PUBLICATIONS

UV Antimicrobial Devices Used to Combat HAIs in Medical Facilities http://www.iuvanews.com/stories/122716/uv-antimicrobial-devics-used-combat-hais.shtml.

*Primary Examiner* — Michael Maskell
(74) *Attorney, Agent, or Firm* — Myron Greenspan Lackenbach Siegel LLP

(57) ABSTRACT

A disinfecting vanity mirror includes a mirror panel having a top end, a bottom end and lateral edges when mounted on a wall. The mirror is moveably mounted on a hinge along one lateral edge mounted to space the panel from the wall to create a plenum space behind the mirror panel to allow air to enter through the bottom end to rise and exit through the top end. A source of UV light is provided in proximity to the plenum space to sanitize the air moving upwardly through the plenum space. A controller is programmed to interrupt or discontinue the generation of UV light when a motion detector senses motion in proximity to the mirror and/or in accordance with a programmed sequence of on and off times for energizing and de-energizing the source of UV light.

19 Claims, 14 Drawing Sheets

Related U.S. Application Data a continuation-in-part of application No. 15/418,231, filed on Jan. 27, 2017, now Pat. No. 9,724,442.

(51) Int. Cl.
*A61L 2/10* (2006.01)
*A47B 67/00* (2006.01)
*A47G 1/02* (2006.01)
*A47G 1/06* (2006.01)

(52) U.S. Cl.
CPC ......... *A61L 2/26* (2013.01); *A47B 2220/0091* (2013.01); *A47G 1/0622* (2013.01); *A61L 2202/11* (2013.01); *A61L 2202/14* (2013.01); *A61L 2202/26* (2013.01); *A61L 2209/111* (2013.01); *A61L 2209/12* (2013.01); *A61L 2209/15* (2013.01)

(58) Field of Classification Search
USPC ................ 250/432 R, 435, 504 R, 492.1
See application file for complete search history.

(56) References Cited

U.S. PATENT DOCUMENTS

| | | | |
|---|---|---|---|
| 8,193,515 B2* | 6/2012 | Kreitenberg | A61L 2/10 250/455.11 |
| 8,662,705 B2 | 3/2014 | Roberts | |
| 8,900,518 B2 | 12/2014 | Seck | |
| 9,308,289 B2* | 4/2016 | Graff | A61L 9/20 |
| 9,480,768 B2 | 11/2016 | Krosney et al. | |
| 9,724,442 B1* | 8/2017 | Munn | A61L 2/10 |
| 2002/0098127 A1* | 7/2002 | Bollini | A61L 9/20 422/121 |
| 2007/0053188 A1 | 3/2007 | New et al. | |
| 2008/0008620 A1* | 1/2008 | Alexiadis | A61L 2/10 422/24 |
| 2009/0041538 A1* | 2/2009 | Berger | E06B 3/9684 403/231 |
| 2009/0291029 A1 | 11/2009 | Ogasawara | |
| 2010/0097013 A1* | 4/2010 | Inskeep | A61L 2/10 315/360 |
| 2010/0296298 A1* | 11/2010 | Martin, Jr. | A45D 42/10 362/311.06 |
| 2012/0199005 A1 | 8/2012 | Koji et al. | |
| 2012/0261593 A1* | 10/2012 | Noori | A61L 2/10 250/492.1 |
| 2013/0214174 A1* | 8/2013 | Domenig | A61L 2/10 250/455.11 |
| 2014/0060104 A1* | 3/2014 | Shur | A61L 2/10 62/264 |
| 2015/0320209 A1* | 11/2015 | Hasselback | H04N 5/2251 348/151 |
| 2015/0360606 A1 | 12/2015 | Thompson et al. | |
| 2016/0074546 A1* | 3/2016 | Rizzone | A61L 2/10 250/455.11 |
| 2017/0007736 A1 | 1/2017 | Engelhard | |
| 2017/0105554 A1* | 4/2017 | Forrest | A47G 1/1686 |
| 2017/0202988 A1* | 7/2017 | Clark | A61L 2/10 |
| 2018/0214595 A1 | 8/2018 | Munn | |

FOREIGN PATENT DOCUMENTS

| | | |
|---|---|---|
| CN | 202908345 | 1/2013 |
| CN | 203633880 | 6/2014 |
| CN | 205561091 | 9/2016 |
| KR | 20120133286 | 12/2012 |

\* cited by examiner

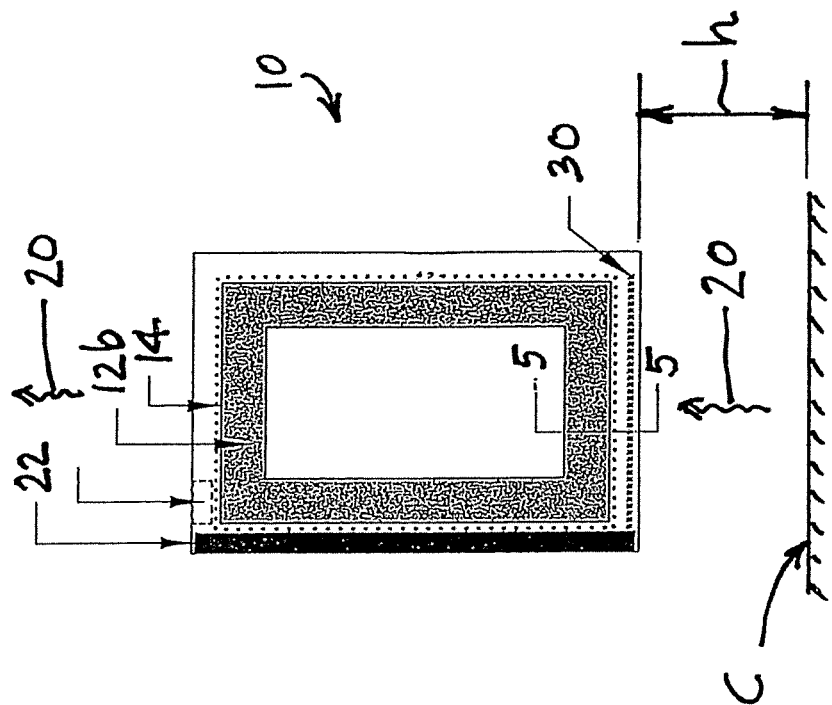
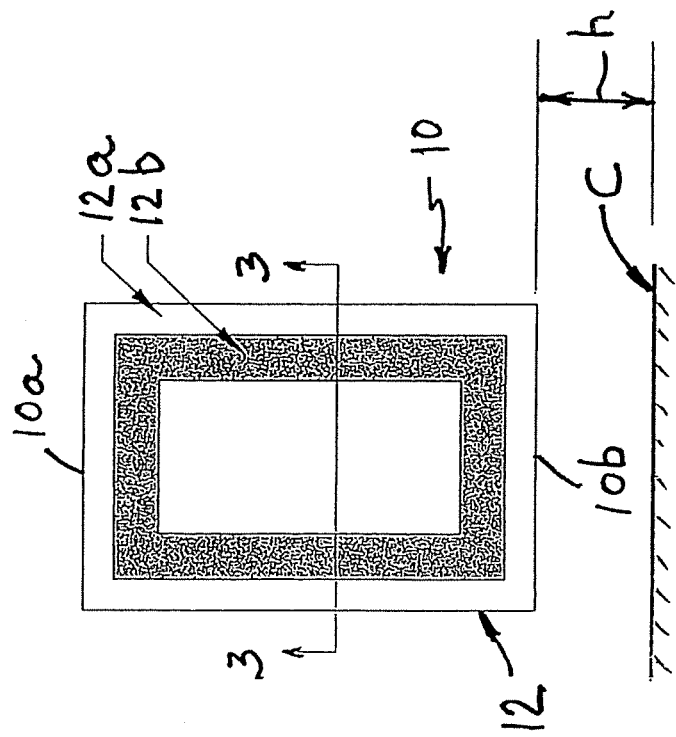
Fig. 2
Fig. 1

DISINFECTING VANITY MIRRORS

CROSS REFERENCE TO RELATED APPLICATIONS

This application is a continuation-in-part of U.S. patent application Ser. No. 15/601,607, filed May 22, 2017 for Hazard-Free Disinfecting Mirrors, which is a continuation-in-part of U.S. patent application Ser. No. 15/418,231, filed Jan. 27, 2017 for Disinfecting Vanity Mirror that issued as U.S. Pat. No. 9,724,442, both of which are hereby incorporated herein by reference.

BACKGROUND OF THE INVENTION

1. Field of the Invention

This invention generally relates to vanity mirrors and, more specifically, to hazard-free vanity mirrors that disinfect and purify air by exposing pathogens to a source of ultraviolet (UV) light within the range of 200-280 nm for use in medical and other facilities.

2. Description of the Background Art

Health care-acquired infections (HAIs) in hospitals, assisted living facilities, etc., are serious health problems. It has been estimated that HAIs cause or contribute in excess of 99,000 deaths annually in the United States. The Center for Disease Control (CDC) reports 1 in 25 patients will contract at least one infection during their stay. Various bacteria become immune or resistant to disinfectants applied to surfaces in hospitals and other medical facilities, these bacterias commonly cause what are being referred to as "staph" infections because they are resistant to many chemical disinfectants used to clean counter tops and other surfaces in hospital rooms and the like. The general problem is discussed, for example, in the Official Publication of the International Ultra Violet Association, IUVANews. http://wwvv.iuva.org/Publications. These infections are considered preventable. In 2011 the federal government stopped reimbursing hospitals for the care of patient that acquired an infection during their stay. Additional penalties for high infection rates have since been added that are in some situations as much as 40% of the overall revenue.

One of the hurdles to success are multi drug resistant organisms (MDRO) that are resistance to standard disinfection products and practices. This has opened the door for new technologies such as ultraviolet germicidal irradiation (UVGI) that primarily uses short-wavelength ultraviolet (UV-C) light to kill or inactivate microorganisms such as bacteria, viruses, molds and other pathogens.

Each year over one million patients contract diseases unrelated to their initial stay at a hospital. Approximately 100,000 Americans die each year for this reason. The cost, both emotionally and financially is staggering and difficult to calculate.

The greatest concentration of pathogens within a hospital room occurs at the surface in the area surrounding the sink in the bathroom. Specifically, the faucet and the handles and the surface between these controls, and the back splash behind the sink, including the wall surface just above the sink is the most infected area in the typical hospital room.

Various UV devices have been proposed to reduce infectious pathogens. For example, bathrooms in airplanes have started to use UV LED strips to reduce pathogens while in flight. Other facilities are being outfitted with various devices to expose pathogens to UV light sources. However, UV light sources have generally been independent or stand alone devices that are specifically designed for intermittent applications.

SUMMARY OF THE INVENTION

In order to address the above and other problems associated with sanitizing or sterilizing airborne pathogens it is an object of the invention to provide a disinfecting vanity mirror that serves the additional function of exposing airborne pathogens and those on surfaces such as countertops to ultraviolet (UV) light to destroy or neutralize such pathogens and makes them ineffective or less effective.

It is another object of the invention to provide a disinfecting vanity mirror as in the previous object that meets infection control requirements and is simple in construction and economical to manufacture.

It is still another object of the invention to provide a disinfecting vanity mirror as in the previous objects that is simple and convenient to install above sinks, countertops and other areas in medical and other facilities that require surface and air purification and disinfection.

It is yet another object of the invention to provide disinfecting vanity mirror of the type under discussion that promotes and accelerates the flow of air to be sanitized or sterilized by heating the air and causing it to rise by convention past a UV source of light.

It is an additional object to the invention to provide a disinfecting vanity mirror that incorporates a UV source of light that is safe to occupants, effective, non-obtrusive and aesthetically pleasing and provides continuous and reliable anti-bacterial sanitizing action both by being in proximity to a countertop and by re-cycling air to insure enhanced exposure of the bacteria to UV radiation.

It is still an additional object of the invention to provide a method of sanitizing or disinfecting airborne bacteria and surfaces by incorporating a UV source of light along a bottom edge of a vanity mirror above a sink and/or countertop (e.g. 10" above the surface) or in other areas or surfaces that require sanitizing or disinfecting.

It is yet an additional object to pivotally mount the vanity mirror along one vertical edge so that it can be pivoted away from the mounting surface to provide access for cleaning that normally covered or hidden surface.

To achieve the above objects and others that will become evident hereinafter, a disinfecting vanity mirror in accordance with the invention comprises a mirror panel having a top end and a bottom end when mounted on a wall. Mounting means is provided for mounting the mirror panel on a vertical surface above a counter top, sink etc. A source of downwardly directed UV light is provided below the vanity mirror to expose pathogens on sinks or countertops to the UV light. The UV light source should be arranged to provide at least downwardly-directed UV light to produce line-of-sight exposure of the UV radiation to pathogens below and around the space below the mirror unit including sinks and counter tops.

A method in accordance with the invention comprises the steps of disinfecting or sterilizing countertop surfaces and air of medical and assisted living facilities, workspaces and other enclosures having vanity mirrors; providing UV light to expose air such as along the lower end of the mirror to expose pathogens in the air and proximate surfaces to the UV-light in the range of 100-280 nm, and preferably within the range of 260-270 nm.

BRIEF DESCRIPTION OF THE DRAWINGS

Those skilled in the art will appreciate the improvements and advantages that derive from the present invention upon reading the following detailed description, claims, and drawings, in which:

FIG. 1 is a front elevational view of a disinfecting vanity mirror in accordance with the present invention;

FIG. 2 is a rear elevational view of the mirror shown in FIG. 1;

DESCRIPTION OF PREFERRED EMBODIMENTS

Figure 3:
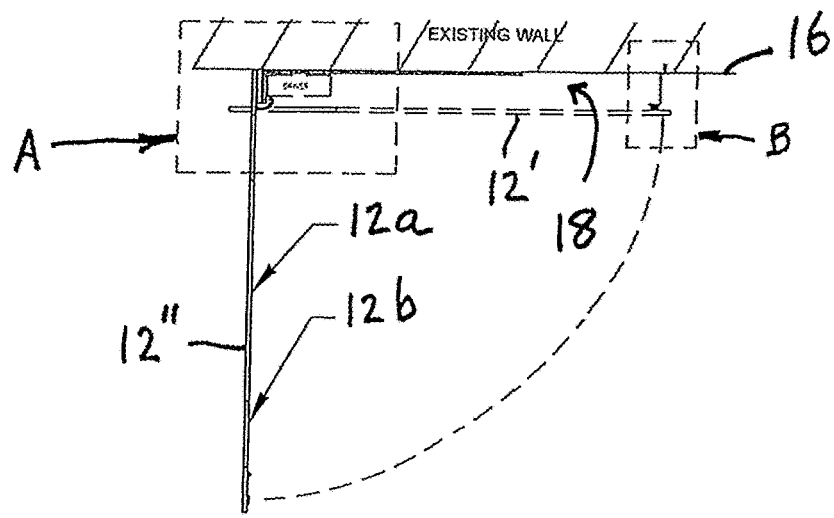
FIG. 3 is a top plan view of the mirror as shown in FIGS. 1 and 2, with the mirror panel in an open position.

The 20 or so most prevalent and dangerous pathogens in hospitals that congregate around sinks and counter-top surfaces can be very significantly reduced when exposed to ultra-violet waves especially in the range of 260-270 nanometers, a fact that is now well documented. The UV diodes that generate this particular wave length (referred to as UVC waves) have in the last few years become commercially available.

The applicant of the subject application has developed and disclosed in patent application Ser. No. 15/418,231, issued as U.S. Pat. No. 9,724,231, a UV generating electrified wall mirror that is also a lighting fixture that is:

a. Aesthetically acceptable;
b. Easy to install;
c. Provides 99.99% destruction of pathogens; when used for approximately 45 minutes over a 24-hour period;
d. Entirely safe;
e. The back of the unit is easily accessible for maintenance and cleaning; and
f. Serves as a both a wall mirror and lighting fixture.

The unit is hinge-mounted, and somewhat similar to the permanently mounted, back lit electrified mirrors currently selling to the hotel industry.

Referring now specifically to the figures, in which the identical or similar parts are designated by the same reference numerals throughout, and first referring to FIG. 1, one embodiment of a disinfecting vanity mirror in accordance with the invention is generally designated by the reference numeral 10.

The mirror 10 is generally rectangular in shape as shown and includes a top end 10a and a bottom end 10b. The mirror 10 includes a mirror panel 12 having a central reflective surface 12a and a frosted peripheral strip 12b. The mirror panel 12 may be ³⁄₁₆" clear hospitality grade mirror. The mirror 10 may be similar in appearance to back-lit mirrors of the type manufactured by MunnWorks LLC in Mount Vernon, N.Y.

LED Strip 14 emitting visible light, for example, at 2700 k provides lighting through the frosted peripheral strip 12b in a conventional manner.

Referring to FIGS. 2-5, the mirror 10 is typically mounted on a wall or vertical surface 16 above a countertop C to create a plenum space 18 between the mirror panel 12 and the mounting surface. The plenum space 18 has openings at the top and bottom ends, 10a, 10b to provide a substantially vertical air shaft, passageway or column for air to rise by entering through the bottom end 10b and exiting through the top end 10a as suggested by the arrows 20 in FIG. 2. While the height of the mirror 10 above the countertop C is not critical a typical height of 10" is typical and will provide beneficial germicidal results in the application of the invention.

Referring specifically to FIGS. 3-6, a method of mounting the mirror 10 is illustrated. A mirror hanger 22 is provided that includes a major mounting portion 22a and a minor mounting portion 22b. As indicated, the major mounting portion 22a is generally coextensive with the wall 16 while the minor mounting portion 22b is provided at one lateral side of the major mounting portion and projects in an outward direction generally normal to the major mounting portion away from the wall 16 when mounted on the wall. Provided along the vertical free edge of the minor mounting portion 22b is a hinge 24 to movably mount the mirror panel 12 between a normally closed position 12', shown in dash outline, substantially parallel to the wall to create the plenum space 18 and an open position 12", shown in solid line in FIGS. 3 and 4, to provide access to the plenum space 18. In the embodiment shown, the mirror panel 12 is spaced a distance d approximately 2" from the wall 18 to provide the plenum space 18 with a depth somewhat less than the dimension d.

Figure 4:
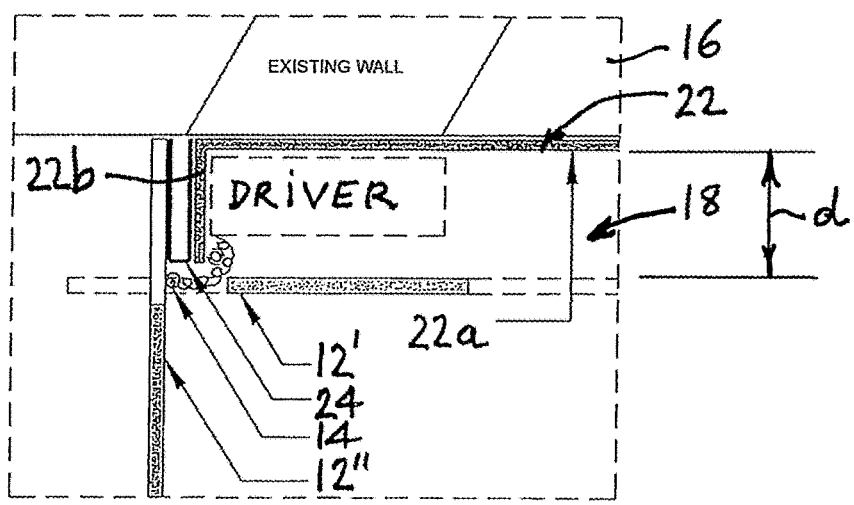
FIG. 4 is an enlarged view of detail A shown in FIG. 3.
Figure 5:
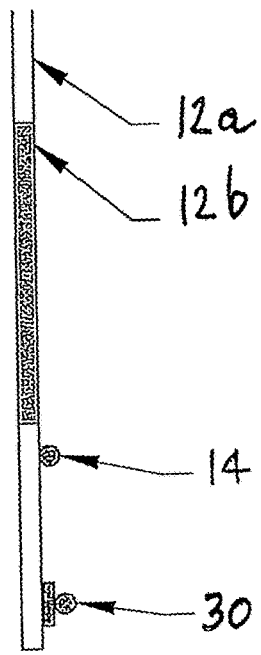
FIG. 5 is an enlarged fragmented cross-sectional view of the lower region of the mirror shown in FIG. 2, taken along line 5-5.
Figure 6:
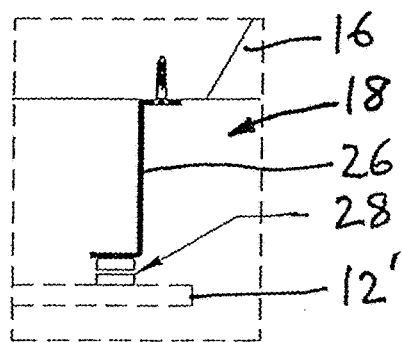
FIG. 6 is an enlarged view of detail B shown in FIG. 3.

Any suitable or conventional hinge can be used to mount the mirror panel 12. However, as shown in FIG. 4, a U-shaped plastic hinge 24 is preferred for this application to eliminate or minimize the number of interstices or crevasses in which pathogens can become lodged and multiply. In order to maintain the mirror panel 12 in its normally closed position parallel to the wall 18 a suitable stopper or spacer 26 is provided that maintains the position of the minor panel in its closed position at spacing d from the wall 18 to keep the mirror panel in a desired position and to ensure the integrity of the plenum space 18. The spacer or stopper 26 is shown to include a magnet 28 on the mirror panel 12 to prevent inadvertent movement of the mirror panel from its closed position.

A feature of the mirror 10 is the integration of a source of UV light 30 that extends along at least a portion but preferably along the entire width of the bottom end 10b to promote convection of air by locally heating air proximate to the bottom end 10b to generate airflow 20. The UV light sanitizes air moving upwardly through the plenum space 18, created to simulate a chimney effect, and promote movement of air past the UV light source 30. Also, by providing the UV light source 30 in proximity to the lower end or edge of the mirror 10 the UV light will be efficient in sanitizing or neutralizing pathogens on the countertop C.

The UV light source 30 is in the form of a strip of LEDs that emit UV light within the range of 200-280 nm and, preferably within the range of 240-280 nm. As indicated in the IUVANews publication ultraviolet radiation is defined most broadly as consisting of radiation within the range of 10-400 nm. However, most effective for germicidal applications is the short wave ultraviolet light normally designated as UV-C. UV-C includes wavelengths of 100-280 nm, although 240-280 nm are most effective for sanitizing or sterilizing airborne pathogens. UV light in that range is most efficiently absorbed by DNA, with maximum absorption being at approximately 260 nm. UV-C has been used for air purification, sterilization and disinfection. High intensity UV at 240-280 nm radiation can destroy DNA in living micro organisms. The effectiveness of the UV radiation is directly related to intensity and exposure time. The present disinfecting vanity mirror 10 is convenient, inexpensive and an effective way to neutralize micro-organisms and pathogens by constantly circulating and recycling the air that passes through the plenum space 18, forcing the air to be continuously exposed to the UV LED-strip 30.

Figure 8:
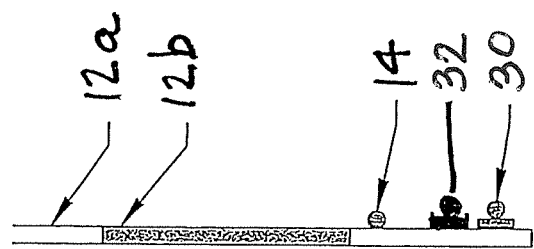
FIG. 8 is similar to FIG. 5 but of the mirror shown in FIG. 7, taken along line 8-8.
Figure 7:
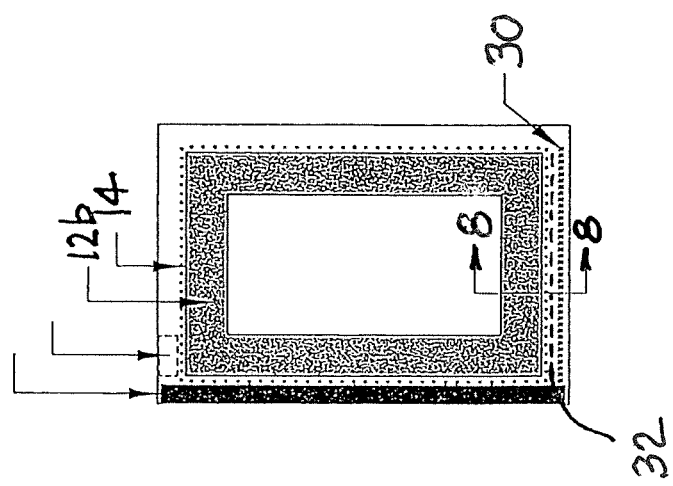
FIG. 7 is a rear elevational view of an alternate embodiment of a disinfecting vanity mirror in accordance with the present invention.

To enhance the quantity of air moved through the plenum space 18 the mirror 10 advantageously utilizes a thermal strip 32, shown in FIGS. 7 and 8, for providing additional heating of the air in proximity to the UV LED strip 30 at the bottom end 10b of the mirror. Between the heating of the air by the UV LED strip 30 and the thermal strip 32 the air below the vanity mirror 10 is heated more quickly and more vigorously and to a higher temperature. This causes higher quantities of air to move up through the plenum space 18 thereby exposing increased numbers of pathogens to the UV light source 30.

By using a mirror 10, for example, that is 24-30" wide and 34-40" tall at a height of approximately 10" above a sink or countertop C most harmful pathogens can be neutralized if power is applied for only approximately 30 minutes per day. The LED strips are conventionally powered when a wall switch is turned on (e.g. in a bathroom where a sink, countertop and vanity mirror are typically situated). Normally the vanity is used at least 30 minutes per day.

The disinfecting vanity mirror 10 is, therefore, an inexpensive and reliable way of exposing air contaminated with pathogens to UV-C light on an ongoing or continuing basis when energized to increase the effectiveness of the sanitization and decontamination of airborne and surface of microorganisms found on countertops.

By locating the UV light source 30 along the bottom edge of the mirror, behind the mirror panel 12, a number of advantages are achieved. The user is protected from UV radiation that can be harmful to the user's eyes and skin. Also, the light does not reflect onto the mirror to avoid undesirable shades or tones or lighting distortions. Using LED light strips considerably increases the life of the sources over conventional UV sources, such as mercury lamps or bulbs. By integrating the UV light source into the vanity mirror there is no need to have an operator use specialized UV equipment to periodically sanitize a facility.

The method of using the mirror 10 is to position a mirror panel 12 a predetermined space from a wall of a medical facility, work space or other chamber where vanity mirrors are utilized to create a plenum space 18 behind the mirror. UV light is then provided at the lower end of the mirror to heat the air and cause it to rise through the plenum space and expose pathogens in the air to the UV light in the range of 10-400 nm and generally 240-280 nm. An optimum wavelength is in the range of 260-270 nm for maximum effectiveness.

The method advantageously includes the additional step of providing enhanced heating of the air to promote movement of the air through the plenum space. This accelerates exposure of the air to be disinfected or sterilized to the UV light. This can be achieved by placing a thermal strip at the lower end of the mirror.

Figure 9:
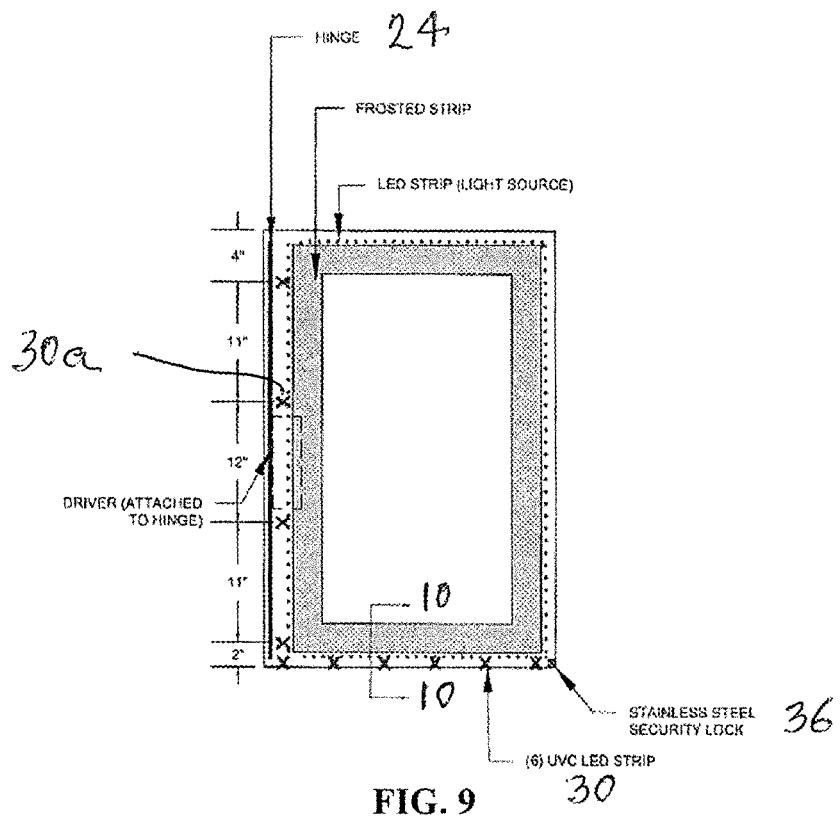
FIG. 9 is similar to FIG. 2 but shows an alternate embodiment in which the UV-LED strip also extends along the vertical hinge to sanitize bacteria that may accumulate on or in proximity to the hinge.
Figure 10:
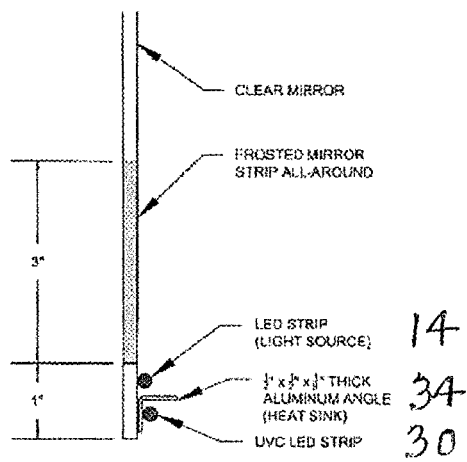
FIG. 10 is an enlarged cross sectional view of the embodiment shown in FIG. 9, taken along 10-10 also showing an aluminum angle attached to the mirror that serves as a heat sink for the UV-LED strip.
Figure 11:
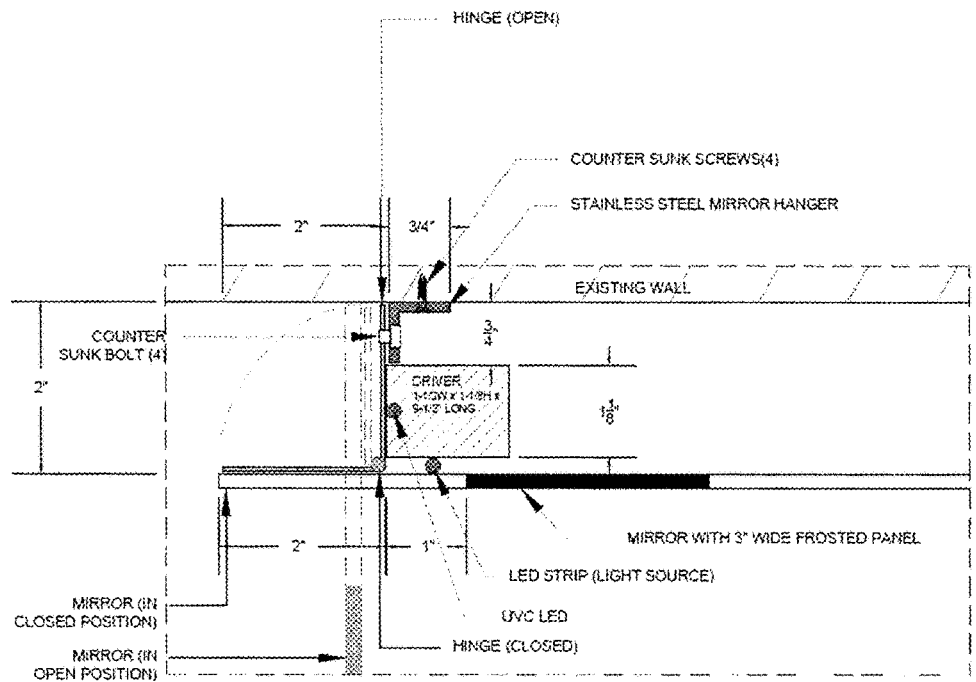
FIG. 11 is a partial top plan view of the embodiment shown in FIG. 9, illustrating a location for the vertical UV-LED strip that extends along the hinge.

Referring to an alternate embodiment shown in FIGS. 9-11, an additional UV-LED strip 30a is shown provided along the vertical edge of the mirror proximate to the hinge 24, the additional UV-LED strip 30a serving to sanitize bacteria that may have attached to the surface of the hinge since the hinge is not always as easily manually cleaned or sanitized, the action of the UV-LED strip 30a ensures that the hinge remains bacteria free with or without manual maintenance. An aluminum angle 34 is shown mounted on the lower edge of the mirror where the UV-LED strip is secured. The angle 34 serves as a heat sink to prevent excessive heat from developing in the UV-LED strip 30 to promote reliability and longevity of the UV-LED strip by preventing excessive heat buildup.

In FIG. 11 the location of the vertical UV-LED strip 30a is shown in relation to the hinge, preferably approximately midway the exposed internal surface of the hinge where buildup of bacteria is most likely and manual maintenance may be most problematic.

Figure 12:
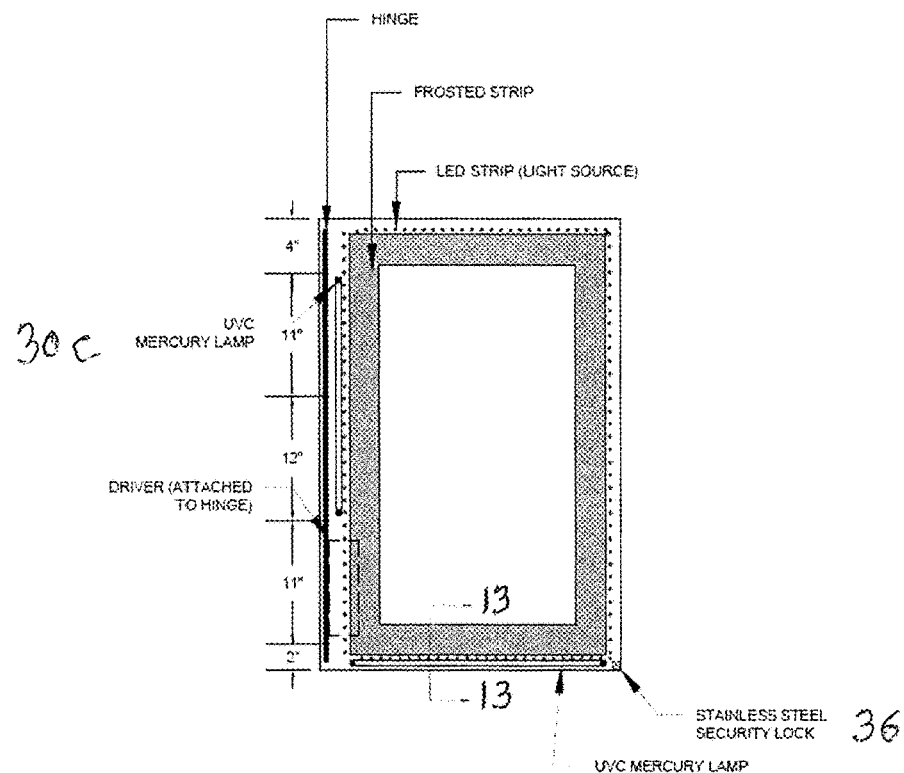
FIG. 12 is similar to FIGS. 2 and 9 showing an additional embodiment in which UV mercury lamps are utilized instead of the UV-LED strips, such lamps being provided along the lower edge of the mirror and along one side of the mirror proximate to the hinge.
Figure 13:
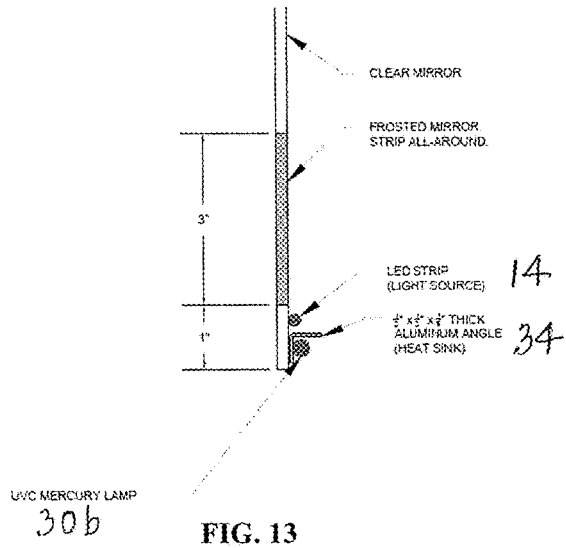
FIG. 13 is an enlarged cross sectional view of the embodiment shown in FIG. 12, taken along line 13-13, showing the UV mercury lamp and the heat sink for removing excess heat from the UV mercury lamp.

Referring to FIGS. 12 and 13, a still further embodiment is illustrated similar to the embodiment shown in FIGS. 9-11, with the exception that the UV-LED strips are replaced by UV mercury lamps or bulbs in the form of miniature florescent tubes that can be mercury lamps, xenon lamps or any lamp with UV wave generating components, waves or light. The invention contemplates the use of any UV source that generates suitable UV light behind a mirror in order to disinfect the area behind the mirror as well as in proximity to the mounting hinge.

In view of the foregoing, the present invention broadly contemplates an electric backlit mirror that is attached to a wall with a hinge for ease of movement to expose and disinfect the surface of the back of the mirror and the wall behind the mirror as well as disinfect the hinge that mounts the mirror in spaced relationship to the wall on which it is mounted. In this connection the driver, electronics, LED diodes, UV diodes, UV light bulbs, tubes or lamps may all be mounted on the mirror itself, allowing the wall behind the mirror to be free of any attachments other than the metal angle that carries the mirror. This facilitates and promotes the manual disinfecting of the entire wall behind the mirror where bacteria is likely to deposit.

Figure 14:
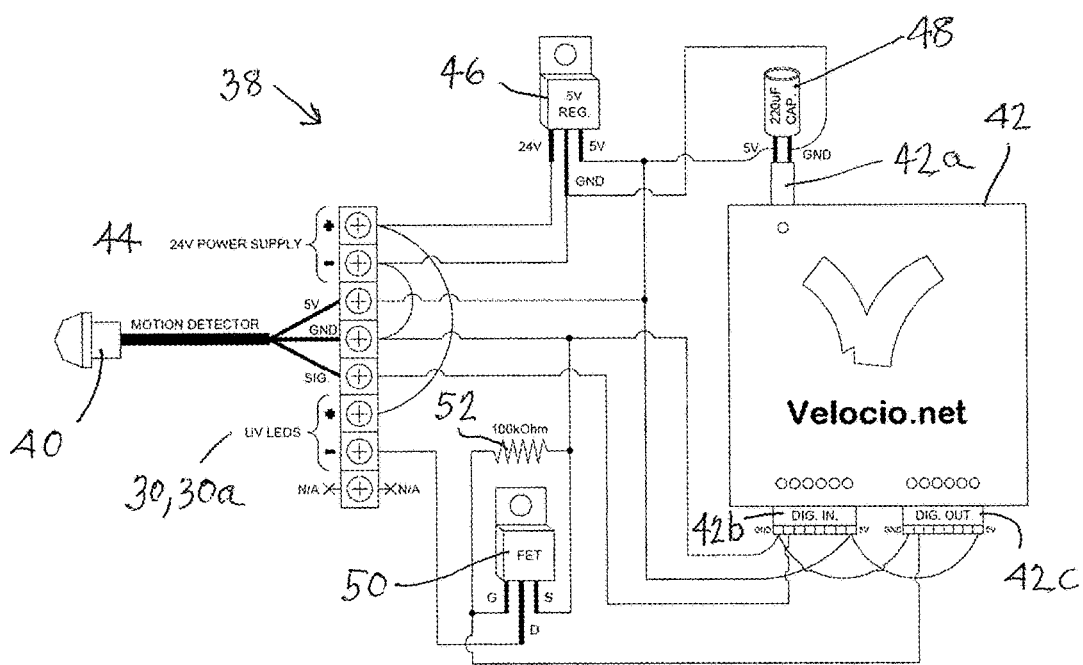
FIG. 14 is a schematic diagram of a motion control wiring circuit that can be used in connection with the aforementioned disinfecting vanity mirror embodiments for controlling or limiting excess emission of UV light to protect individuals in proximity to the mirrors.

To avoid potential safety hazards to patients and occupants of the enclosures in which the mirrors are mounted from excessive exposure to UV light, and in order to comply with governmental and/or hospital regulations, the mirrors of the invention may be provided with circuitry for intermittently de-activating or interrupting the UV light sources or generators so that these are not always on to emit UV light continuously but intermittently but sufficiently to be effective for sanitizing or disinfecting the areas within the enclosure. Referring to FIG. 14, a circuit 38 is shown that can be used for this purpose. The circuit 38 is preferably also mounted behind the mirror, possibly encapsulated, to minimize the openings, traps or surface areas on which bacteria can settle and grow. Circuit 38 serves two purposes. The first is to cycle the UV light sources (e.g. 30 and 30a) in accordance with a desired or predetermined schedule, and the second is to detect motion within the enclosure where the mirror is mounted so that the UV light sources can be de-activated, interrupted or de-energized when motion in proximity to the mirror is detected. Any programmed controller can be used to provide these functions. Circuit 38, by way of example, illustrates the use of a motion detector 40 connected to a programmed controller 42. A power supply 44, such as a 24 volt source, is used to energize the circuit 38, a 5 volt regulator being used, if necessary, to generate a regulated voltage to power the programmed controller 42. A capacitor 48 connected to the controller 42 at port 42a, a field effect transistor (FET) 50 and resistor 52 are connected to input port 42b and output port 42c of the programmed controller as shown. The UV LED light sources 30, 30a are connected as shown, the components connected to the programmed controller 42 enabling the controller 42 to operate as a timer to establish predetermined time intervals, as to be described in connection with FIG. 15. FIG. 14 however, is only one configuration of a programmed controller for timing the operation of the UV-LED's although any other known timers or timing circuits may be utilized for this purpose.

Figure 15:
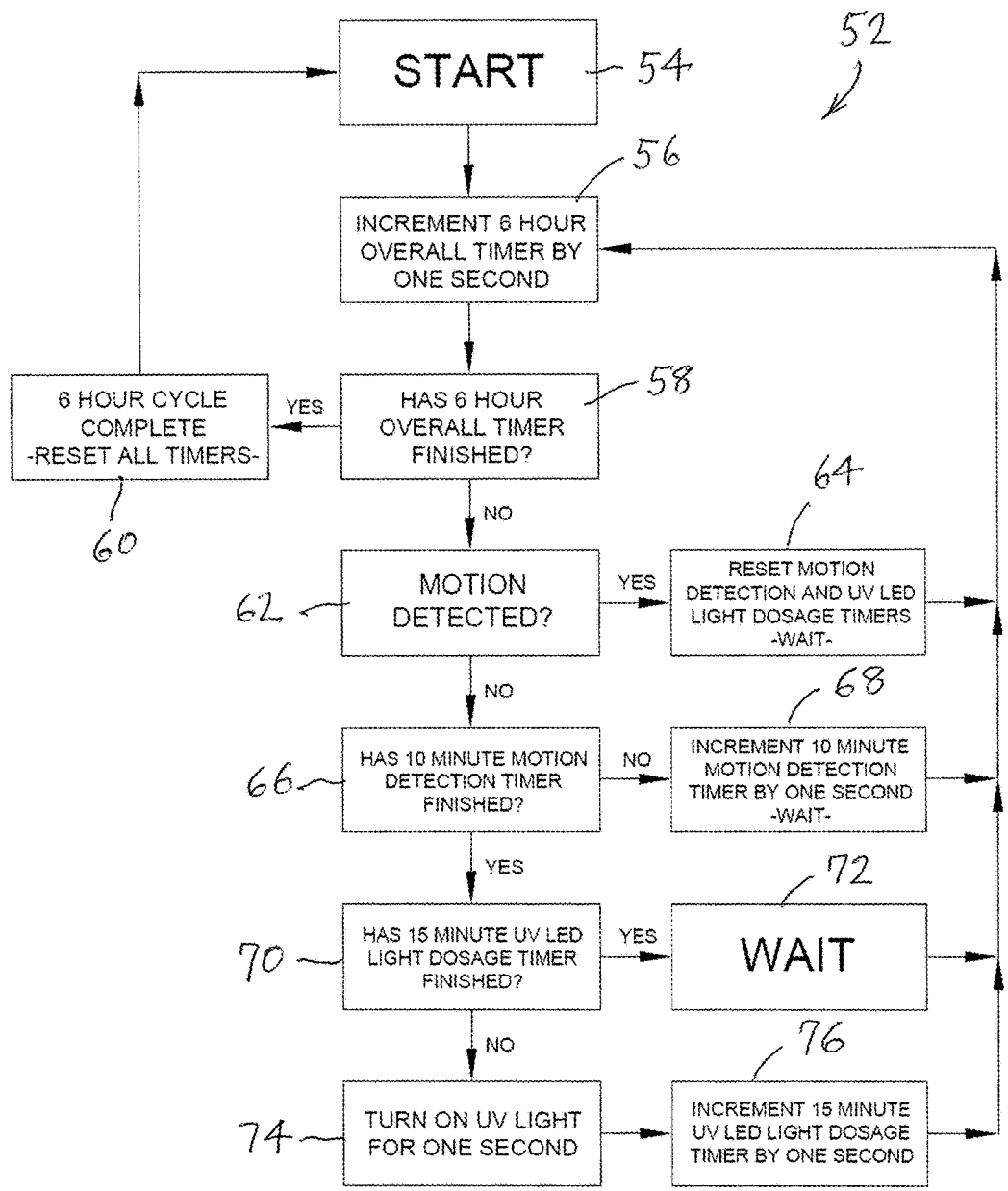
FIG. 15 illustrates a flow chart representing the operation of the programmed controller in FIG. 14 for controlling and preventing excess emission of UV light with the circuit shown in FIG. 14.
Figure 16:
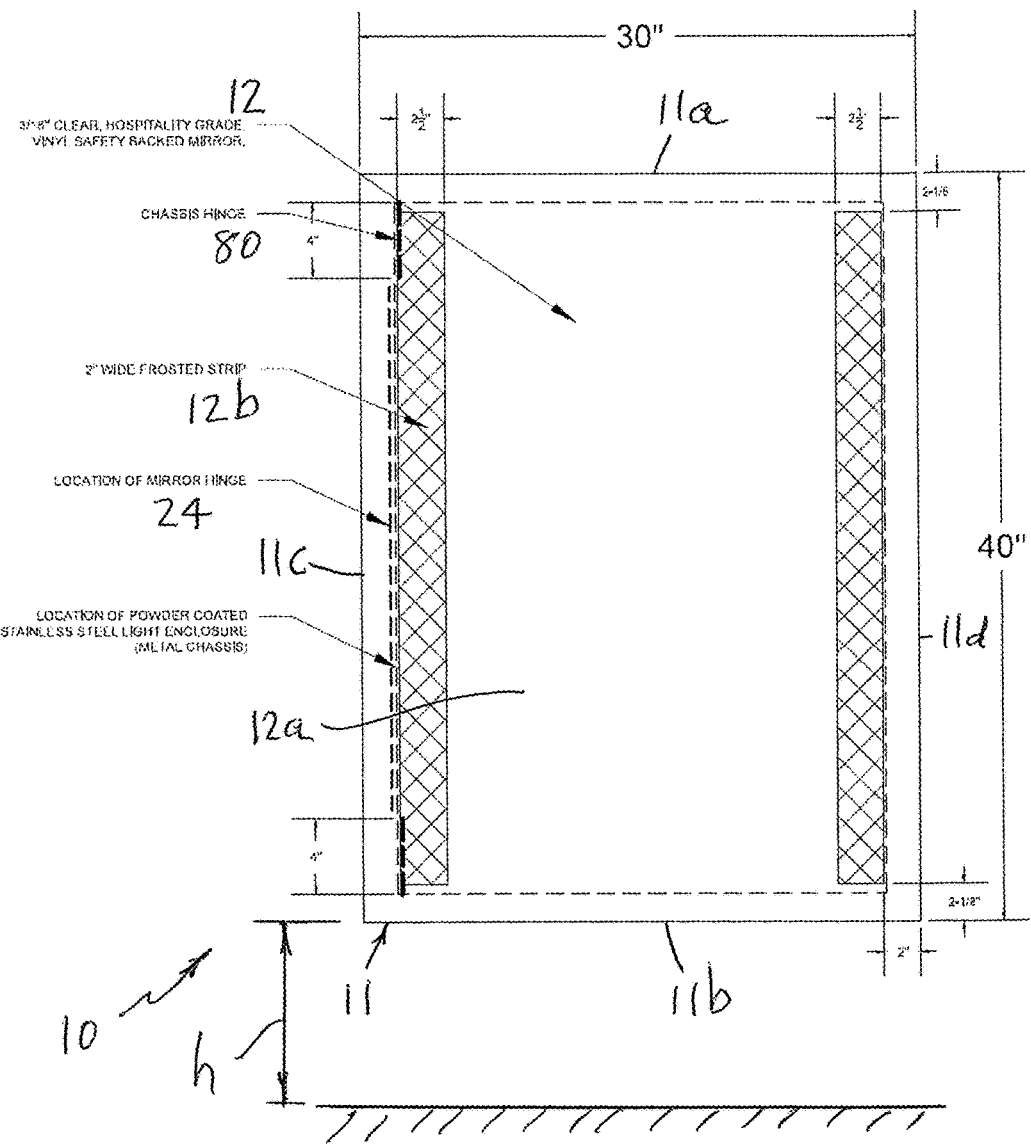
FIG. 16 is a front elevational view of a further embodiment of the invention that is mounted directly and juxtaposed on a wall surface without creating a plenum space.

Referring to FIG. 15, a flow chart 52 is shown that illustrates the programmed protocol or logic for monitoring and controlling the UV light sources, whether they be LED's, lamps, bulbs, florescents, etc. Initially, the controller 42 commences operation at 54 to increment the timer in 6 hour intervals at 56. Thus, without external influences, the controller energizes the UV light sources every 6 hours. The UV light sources are energized four times during each 24 hour period. At 58, the controller 42 queries whether the 6 hour timer has completed its 6 hour interval. After a 6 hour cycle has been completed all the timers are reset at 60 and the controller reverts to the start position at 54. If the 6 hour overall timer has not been completed the controller queries whether the motion detector 40 has detected any motion, at 62. If motion has been detected the motion detection and UV-LED light dosage timers are reset, at 64, and the controller reverts to incrementing the 6 hour overall timer, at 56, to repeat the protocol. If motion has not been detected at 62 the controller queries whether a 10 minute motion detection timer has finished, at 66. If the motion detection timer has not finished the 10 minute motion detection timer is incremented by one second at 68 and the controller reverts to increment 6 hour overall timer at 56. If the 10 minute motion detection timer has finished, at 66, the controller 42 queries whether the 15 minute UV-LED light dosage timer has finished, at 70. If it has finished the controller is instructed to wait, at 72, after which the 6 hour overall hour is incremented by one second, at 56. If the 15 minute UV-LED light dosage timer has not finished, at 70, the UV light sources are turned on for one second, at 74. After the UV light has been activated, at 74, the 15 minute UV-LED timer is incremented by one second, at 76, and the 6 hour overall timer is thereafter incremented again at 56. The cycle is repeated on an ongoing or continuous basis with the program controller 42 regulating the operation or energization of the UV light sources at the preselected or desired time intervals, as may be modified by the presence of individuals sensed by the motion detector 40.

Figure 17:
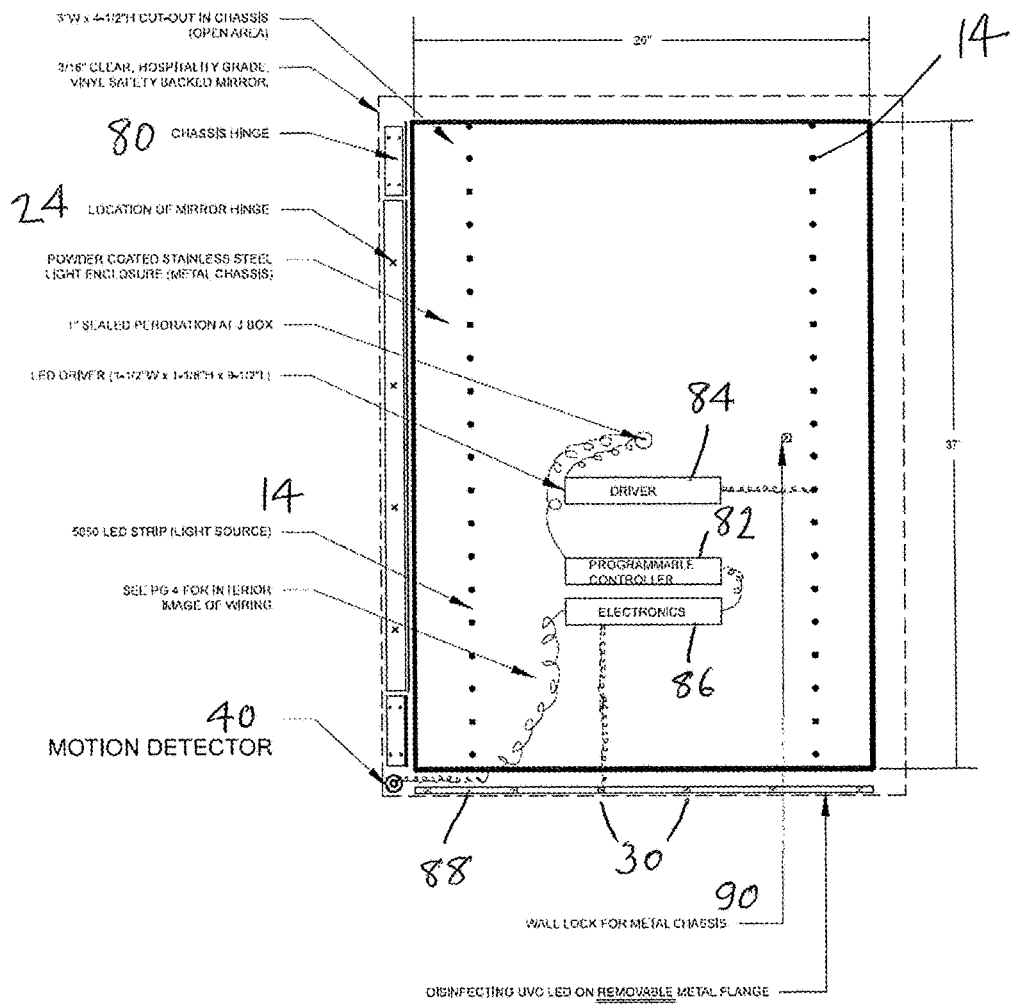
FIG. 17 is similar to FIG. 16 with the mirror panel removed to expose the electronics including LED light strips, UV light strips and control circuitry.
Figure 18:
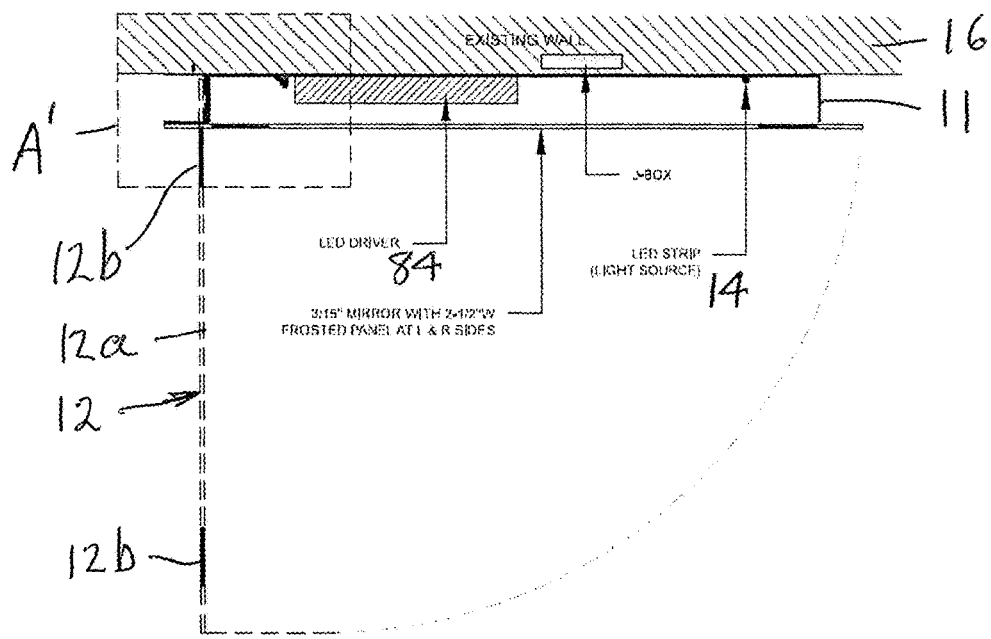
FIG. 18 is a top plan view of the embodiment shown in FIGS. 16 and 17, with the mirror panel in the open position to provide access to the interior of the cabinet.
Figure 19:
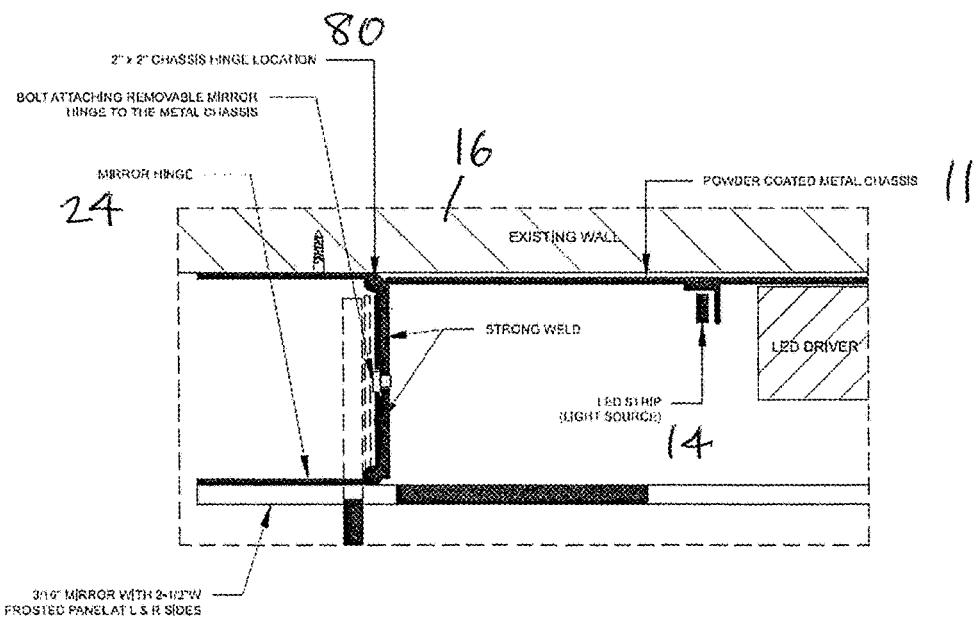
FIG. 19 is an enlarged detail A' shown in FIG. 18.
Figure 20:
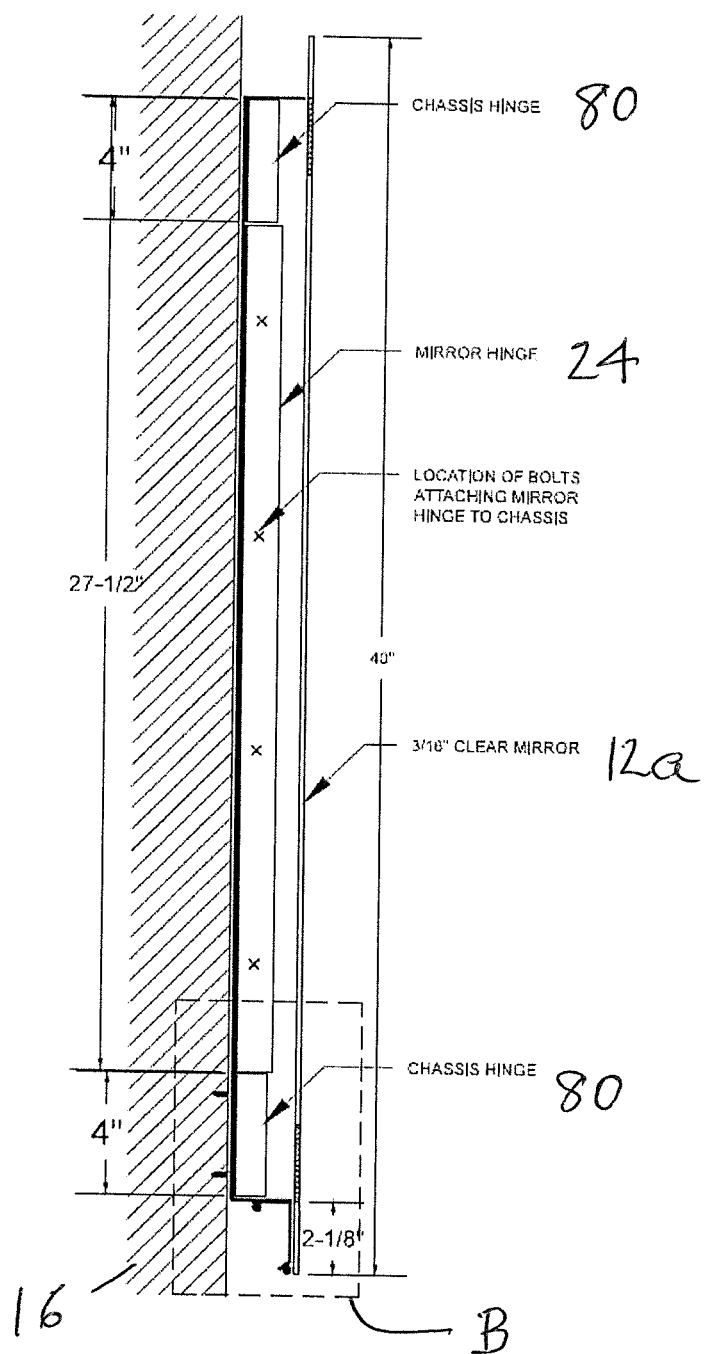
FIG. 20 is a side elevational view, in vertical section, of the cabinet shown in FIGS. 16 and 17.
Figure 21:
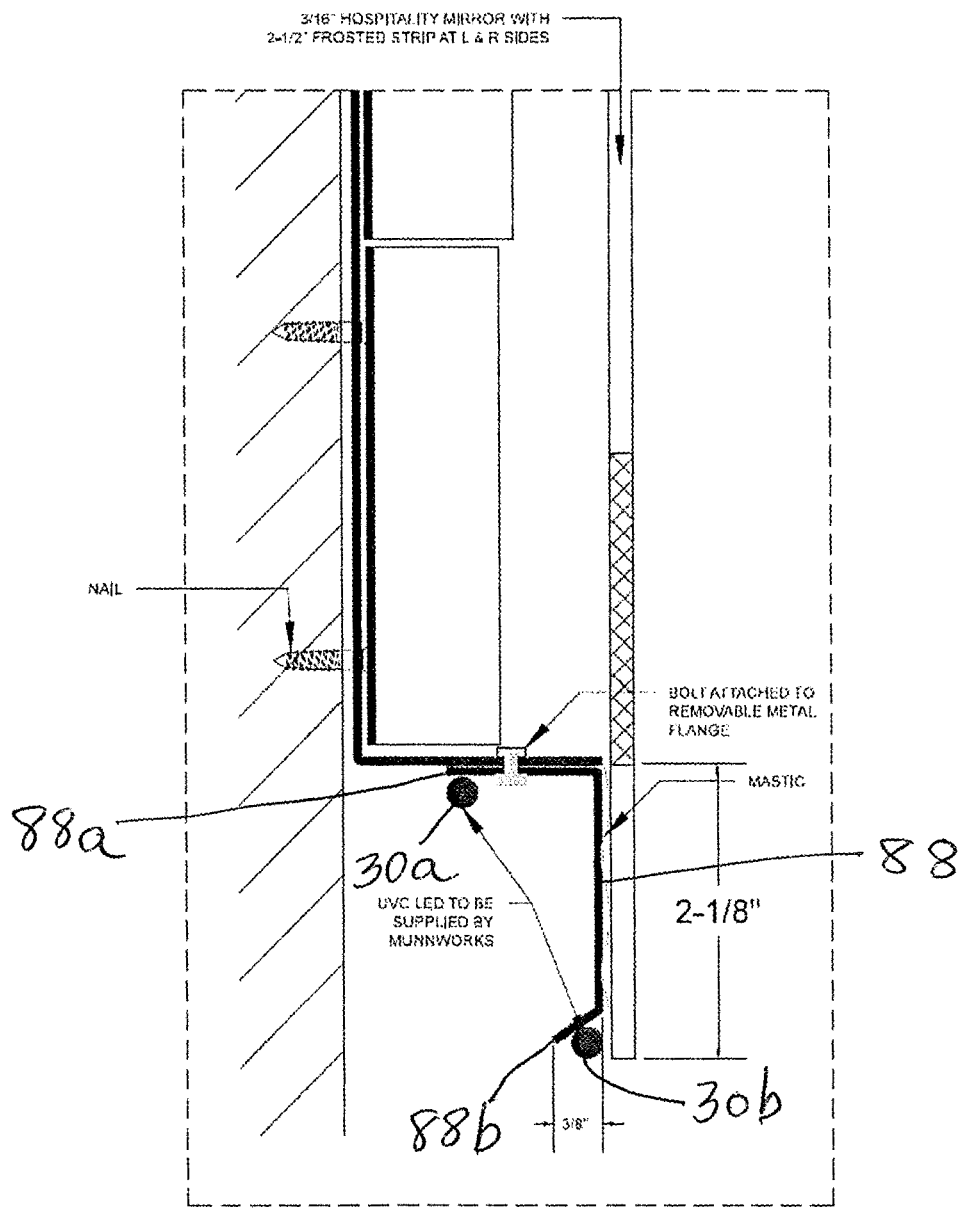
FIG. 21 is an enlarged detail B shown in FIG. 20.
Figure 22:
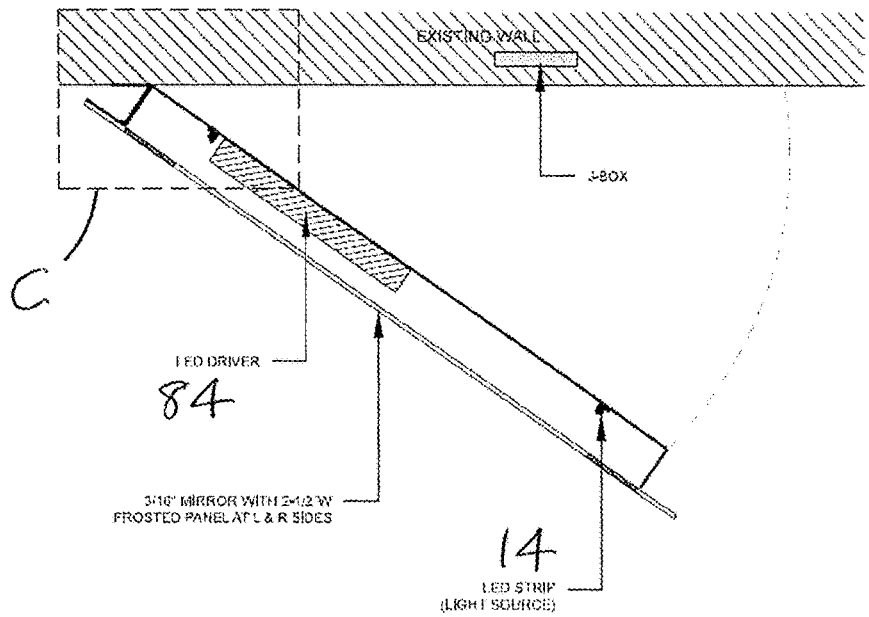
FIG. 22 is similar to FIG. 18, showing the cabinet in a pivoted position to provide access to the surface normally covered by the cabinet.
Figure 23:
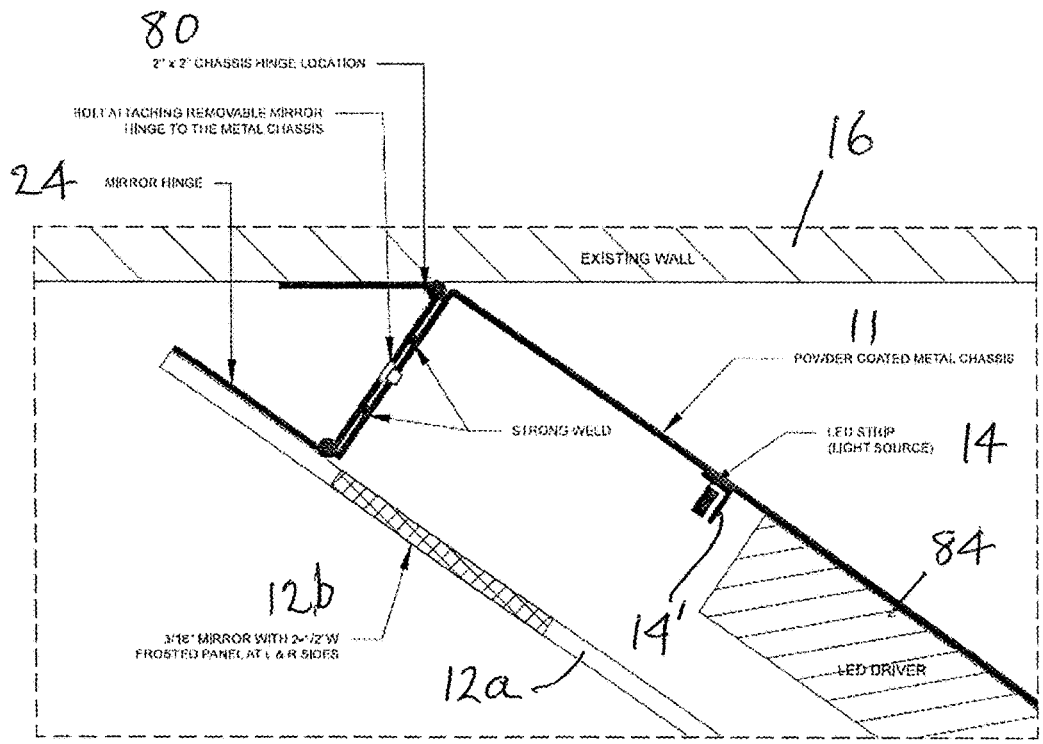
FIG. 23 is an enlarged detail C shown in FIG. 22.

Referring to FIGS. 17-23 another embodiment of the disinfecting vanity mirror in accordance with the invention includes a cabinet 11 having top, bottom and side lateral ends or edges 11a-11d, respectively. The mirror panel 12 is mounted on a cabinet "and at least one UV light source is mounted on the bottom end of the cabinet", the UV light source being configured to direct UV light vertically downwardly to sanitize air and surfaces below the mirror panel. The vanity mirror 10 is provided with a chassis hinge 80 that enables the pivoting of the cabinet to a position or juxtaposed against the mounting surface or wall in close proximity thereto as shown, for example, in FIGS. 18-21. However, the hinge 80 allows the cabinet 11 to be pivoted away from the wall mounting surface as shown in FIGS. 22 and 23 to provide access to the surface normally covered by the cabinet when in the closed position. This allows the surface behind the cabinet to be cleaned and disinfected periodically or as often as necessary. Referring to FIG. 17, with the mirror panel removed, a programmable controller 82 is connected to the LED light strips 14, controlled by the programmable controller 82. Electronics 86 shown in FIGS. 14 and 15 receive input from motion detector 40 and suitably actuates the UV LEDs or light source 30.

A feature of the invention is the provision of a metal flange or bracket 88 running along the bottom end or edge 11b of the cabinet 11 on which there are mounted UV LEDs, as shown in FIGS. 17 and 20-21. The number of the UV LEDs and the power of these LEDs are selected to provide the desired UV intensity on a countertop or surface C, keeping in mind that the UV intensity is inversely propositional to the square of the distance, rapidly increasing at distances less than 1 meter. Directing the UV light downwardly or substantially downwardly increases the UV dose for effectiveness. Also, since dust and films that become deposited on the UV light sources lowers UV output these UV LEDs should normally be cleaned periodically. Also, a suitable fan or the like can be provided to blow air on the LEDs to keep them free of dust.

Referring to FIG. 17 a wall lock is provided for selectively maintaining the cabinet chassis in its closed or retracted position against the wall or mounting surface to prevent the cabinet to be inadvertently pivoted outwardly as shown in FIGS. 22 and 23.

Another feature of the invention is the provision of removable metal flange 88 shown in FIGS. 17, 20 and 21. The flange or bracket is generally L-shaped in cross section and extends substantially across the entire width of the bottom end 11*b* of the cabinet. The flange or bracket 88 has free edges 88*a* and 88*b* as shown in FIG. 21 and one UV light source including spaced UV LEDs are mounted generally along each of the free edges 88*a*, 88*b* of the flange or bracket 88. This ensures that the UV LEDs direct UV light substantially vertically downwardly to sanitize air and surfaces C below the vanity mirror.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. Disinfecting vanity mirror comprising a cabinet having a top end, a bottom end and lateral edges when mounted on a wall; a mirror panel mounted on said cabinet; mounting means for mounting said cabinet on the wall; and at least one exposed UV light source mounted on said bottom end, the UV light source being configured to direct UV light at least substantially vertically downwardly to sanitize air and surfaces below the vanity mirror, said mounting means including a hinge at one of said one lateral ends to movably mount said cabinet between a normally closed position substantially juxtaposed against the wall and an open position to provide access to a surface normally covered by said cabinet when in said closed position, said hinge enabling independent movement of said cabinet and said mirror panel relative to said cabinet whereby said normally covered surface can be cleaned and disinfected when said cabinet is moved to said open position.

2. A vanity mirror as defined in claim 1, wherein said mounting means includes a hinge at one of said one lateral edges to movably mount said cabinet between a normally closed position substantially juxtaposed against the wall and an open position to provide access to a surface normally covered by said cabinet when in said closed position, whereby said normally covered surface can be cleaned and disinfected.

3. A vanity mirror as defined in claim 1, further comprising a wall lock for normally retaining said cabinet in said closed position and selectively enabling movement of said cabinet to an open position to expose said normally covered wall surface.

4. A vanity mirror as defined in claim 1, wherein said source of UV light comprises a plurality of UV-generating LEDs.

5. A vanity mirror as defined in claim 1, wherein said source of UV light generates ultraviolet radiation within the range of 200-280 nm.

6. A vanity mirror as defined in claim 5, wherein the UV radiation is in the range of 240-280 nm.

7. A method of disinfecting or sterilizing air and surfaces in medical facilities, workspaces and other chambers having vanity mirrors including a cabinet comprising the steps of mounting a vanity mirror having a bottom end and a mirror panel above at least one of a sink and counter-top surface; and providing at least two exposed UV light sources mounted on said bottom end of said cabinet, one UV light source being arranged to direct UV light substantially vertically downwardly and another UV light source being arranged to direct UV light at least partially downwardly and at least partially outwardly in a direction away from a surface on which said cabinet is mounted to sanitize air and surfaces below and generally in the lower proximity of said mirror panel.

8. Disinfecting vanity mirror comprising a cabinet having a top end, a bottom end and lateral edges when mounted on a wall; mounting means for mounting said cabinet along one lateral edge on a vertical surface; at least one exposed UV light source mounted on said bottom end of said cabinet, the UV light source being configured to direct UV light at least substantially vertically downwardly to sanitize air and surfaces in below said mirror panel; and control means for controlling and intermittently discontinuing the generation of UV light to limit the extent to which people in proximity to the mirror may be exposed to UV light further comprising a flange or bracket extending generally along said bottom end, said at least one UV light source being mounted on said flange or bracket that is configured to direct UV light substantially downwardly and away from said cabinet.

9. A vanity mirror as defined in claim 8, wherein said control means includes a motion detector.

10. A vanity mirror as defined in claim 8, wherein said control means includes a programmable controller.

11. A vanity mirror as defined in claim 8, wherein said control means includes a timer.

12. A vanity mirror as defined in claim 8, wherein UV light is selected to be in the range of 240-280 nm.

13. A vanity mirror as defined in claim 8, wherein the UV light is provided by a strip of LEDs in proximity of said bottom end of said mirror.

14. A vanity mirror as defined in claim 8, wherein said mounting means includes a hinge at one of said one lateral edges to movably mount said cabinet between a normally closed position substantially juxtaposed against the wall and an open position to provide access to a surface normally covered by said cabinet when in said closed position, whereby said normally covered surface can be cleaned and disinfected.

15. A vanity mirror as defined in claim 14, further comprising a wall lock for normally retaining said cabinet in said closed position and selectively enabling movement of said cabinet to an open position to expose said normally covered wall surface.

16. A vanity mirror as defined in claim 8, wherein said flange or bracket is removably attached to said bottom end of said cabinet.

17. Disinfecting vanity mirror comprising a cabinet having a top end, a bottom end and lateral edges when mounted on a wall; a mirror panel mounted on said cabinet; mounting means for mounting said cabinet on the wall; at least two UV light sources mounted on said bottom end of said cabinet, one UV light source being arranged to direct UV light substantially vertically downwardly and another UV light source being arranged to direct UV light at least partially downwardly and at least partially outwardly in a direction away from a surface on which said cabinet is mounted to sanitize air and surfaces below and forwardly of the vanity mirror; and a flange or bracket extending generally along said bottom end, said at least two UV light sources being mounted on said flange or bracket.

18. Disinfecting vanity mirror comprising a cabinet having a top end, a bottom end and lateral edges when mounted on a wall; a mirror panel mounted on said cabinet; mounting means for mounting said cabinet on the wall; and at least one exposed UV light source mounted on said bottom end, the UV light source being configured to direct UV light at least substantially vertically downwardly to sanitize air and surfaces below the vanity mirror further comprising a flange or bracket extending generally along said bottom end, said at least one UV light source being mounted on said flange or bracket that is configured to direct UV light substantially downwardly and away from said cabinet.

19. A vanity mirror as defined in claim 18, wherein said flange or bracket is removably attached to said bottom end of said cabinet.

* * * * *